US00PP16211P2

(12) United States Plant Patent
Smith

(10) Patent No.: US PP16,211 P2
(45) Date of Patent: Jan. 24, 2006

(54) ***CHRYSANTHEMUM* PLANT NAMED 'YOSHARON'**

(50) Latin Name: *Chrysanthemum×morifolium*
Varietal Denomination: Yosharon

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 94 days.

(21) Appl. No.: 10/937,856

(22) Filed: Sep. 8, 2004

(51) Int. Cl.
*A01H 5/00* (2006.01)

(52) U.S. Cl. ..... Plt./292

(58) Field of Classification Search ..... Plt./292
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yosharon', characterized by its upright, outwardly spreading and rounded plant habit; freely branching habit; freely flowering habit; large decorative-type inflorescences with elongated oblong-shaped ray florets; purple-colored ray florets; natural season flowering in mid-September in the Northern Hemisphere; and good garden performance.

2 Drawing Sheets

Botanical classification/cultivar designation: *Chrysanthemum×morifolium* cultivar Yosharon.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yosharon'.

The new cultivar is a product of a planned breeding program conducted by the Inventor in Salinas, Calif. and Alva, Fla. The objective of the breeding program is to create new garden-type *Chrysanthemum* cultivars having inforescences with desirable inflorescence forms, attractive floret coloration and good garden performance.

The new *Chrysanthemum* originated from a cross-pollination made in January, 2000 in Salinas, Calif., of a proprietary *Chrysanthemum×morifolium* seedling selection identified as code number 97-L088, not patented, as the female, or seed, parent with the *Chrysanthemum×morifolium* cultivar Stacy, disclosed in U.S. Plant Pat. No. 11,852, as the male, or pollen, parent. The new *Chrysanthemum* was discovered and selected by the Inventor as a single flowering plant within the progeny of the stated cross-pollination grown in a controlled environment in Alva, Fla. in October, 2000. The selection of this plant was based on its desirable inflorescence form, attractive floret coloration and good garden performance.

Asexual reproduction of the new cultivar by terminal vegetative cuttings in a controlled environment in Alva, Fla. since January, 2001, has shown that the unique features of this new *Chrysanthemum* are stable and reproduced true to type in successive generations.

SUMMARY OF THE INVENTION

The cultivar Yosharon has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yosharon'. These characteristics in combination distinguish 'Yosharon' as a new and distinct cultivar of *Chrysanthemum:*

1. Upright, outwardly spreading and rounded plant habit.
2. Freely branching habit.
3. Freely flowering habit.
4. Large decorative-type inflorescences with elongated oblong-shaped ray florets.
5. Purple-colored ray florets.
6. Natural season flowering in mid-September in the Northern Hemisphere.
7. Good garden performance.

In side-by-side comparisons conducted in Alva, Fla. under natural season conditions, plants of the new *Chrysanthemum* differed from plants of the female parent, the selection identified as code number 97-L088, in the following characteristics:

1. Plants of the new *Chrysanthemum* were smaller and more rounded than plants of the female parent selection.
2. Plants of the new *Chrysanthemum* flowered about one month earlier than plants of the female parent selection.

In side-by-side comparisons conducted in Alva, Fla. under natural season conditions, plants of the new *Chrysanthemum* differed from plants of the male parent, the cultivar Stacy, in the following characteristics:

1. Plants of the new *Chrysanthemum* and the cultivar Stacey differed in inflorescence form as plants of the cultivar Stacy had daisy-type inflorescences.
2. Plants of the new *Chrysanthemum* flowered about ten days earlier than plants of the cultivar Stacy.

3. Plants of the new *Chrysanthemum* and the cultivar Stacy differed in ray floret coloration as plants of the cultivar Stacy had white and purple bi-colored ray florets.

Plants of the new *Chrysanthemum* can be compared to plants of the *Chrysanthemum* cultivar Debonair, disclosed in U.S. Plant Pat. No. 5,324. In side-by-side comparisons conducted in Alva, Fla. under natural season conditions, plants of the new *Chrysanthemum* differed from plants of the cultivar Debonair in the following characteristics:

1. Plants of the new *Chrysanthemum* were smaller and more rounded than plants of the cultivar Debonair.
2. Plants of the new *Chrysanthemum* had larger inflorescences than plants of the cultivar Debonair.
3. Plants of the new *Chrysanthemum* flowered about three days earlier than plants of the cultivar Debonair.

Plants of the new *Chrysanthemum* can also be compared to plants of the *Chrysanthemum* cultivar Cupidores, disclosed in U.S. Plant Pat. No. 12,919. In side-by-side comparisons conducted in Alva, Fla. under natural season conditions, plants of the new *Chrysanthemum* differed from plants of the cultivar Cupidores in the following characteristics:

1. Plants of the new *Chrysanthemum* were more rounded than plants of the cultivar Cupidores.
2. Plants of the new *Chrysanthemum* had smaller inflorescences than plants of the cultivar Cupidores.
3. Plants of the new *Chrysanthemum* flowered more uniformly than plants of the cultivar Cupidores.
4. Plants of the new *Chrysanthemum* flowered about five days later than plants of the cultivar Cupidores.
5. Ray florets of plants of the new *Chrysanthemum* were darker in color than ray florets of plants of the cultivar Cupidores.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproduction of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yosharon' grown in a container.

The photograph on the second sheet comprises a close-up view of typical inflorescences of the cultivar 'Yosharon'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Yosharon.

Commercial classification: Decorative-type garden *Chrysanthemum.*

Parentage:

*Female, or seed, parent.*—Proprietary *Chrysanthemum×morifolium* seedling selection identified as code number 97-L088, not patented.

*Male, or pollen, parent.*—*Chrysanthemum×morifolium* cultivar Stacy, disclosed in U.S. Plant Pat. No. 11,852.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with rounded crown. Stems initially upright, then outwardly spreading. Freely branching with about 14 lateral branches per plant. Moderately vigorous.

*Plant height.*—About 17 cm.

*Plant diameter.*—About 28 cm.

*Lateral branches.*—Length: About 14.5 cm. Diameter: About 5 mm. Internode length: About 1.3 cm. Strength: Strong. Texture: Pubescent. Color: Close to 146A.

*Foliage description.*—Leaf arrangement: Alternate. Length: About 4.9 cm. Width: About 3.8 cm. Apex: Mucronate. Base: Truncate. Margin: Palmately and deeply lobed; sinuses mostly divergent. Texture, upper and lower surfaces: Pubescent. Color: Developing and fully expanded foliage, upper surface: More green than 147A. Developing and fully expanded foliage, lower surface: Close to 147B. Venation, upper surface: Close to 146A. Venation, lower surface: Close to 146A to 146B. Petiole: Length: About 1.7 cm. Diameter: About 3 mm. Texture, upper and lower surfaces: Pubescent. Color, upper surface: Close to 146A. Color, lower surface: Close to 146B.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences hemispherical in shape. Freely flowering habit; about twelve inflorescences develop per lateral branch. Inflorescences persistent. Inflorescences not fragrant.

*Flowering response.*—Under natural season conditions, plants flower in mid-September in the Northern Hemisphere.

*Inflorescence bud (before showing color).*—Height: About 7 mm. Diameter: About 9 mm. Shape: Oblate. Color (lower surface of phyllaries): Close to 147A.

*Inflorescence size.*—Diameter: About 5.2 cm. Depth (height): About 2.3 cm. Disc diameter: No disc florets observed. Receptacle diameter: About 6 mm. Receptacle height: About 6.5 mm.

*Ray florets.*—Shape: Elongated oblong. Length: About 2.5 cm. Corolla tube length: About 5 mm. Width: About 6.5 mm. Apex: Emarginate. Margin: Fused. Texture: Smooth, glabrous; satiny. Surface: Initially concave, with development, convex. Orientation: Initially upright, then perpendicular to the peduncle to reflexed. Number of ray florets per inflorescence: About 205 in numerous whorls. Color: When opening, upper and lower surfaces: 77A. Fully opened, upper surface: 77A to 77B; color becoming closer to 77B to 77C. Fully opened, lower surface: 77C to 77D.

*Phyllaries.*—Quantity per inflorescence: About 24. Length: About 8 mm. Width: About 3 mm. Shape: Deltoid, elongated. Apex: Acute. Base: Truncate, fused. Margin: Entire. Texture, upper surface: Smooth, waxy. Texture, lower surface: Pubescent. Color, upper surface: More green than 147A. Color, lower surface: Close to 147A.

*Peduncle.*—Length: First peduncle: About 4.25 cm. Fourth peduncle: About 6.25 cm. Seventh peduncle: About 9.1 cm. Diameter: About 2.5 mm. Strength: Strong. Aspect: About 45° from vertical. Texture: Pubescent. Color: Close to 146A.

*Reproductive organs.*—Androecium: Not observed. Gynoecium: Present on ray florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good gardem performance and to be tolerant to rain, wind and temperatures ranging from 0 to greater than 38° C.

It is claimed:

1. A new and distinct cultivar of *Chrysanthemum* plant named 'Yosharon', as illustrated and described.

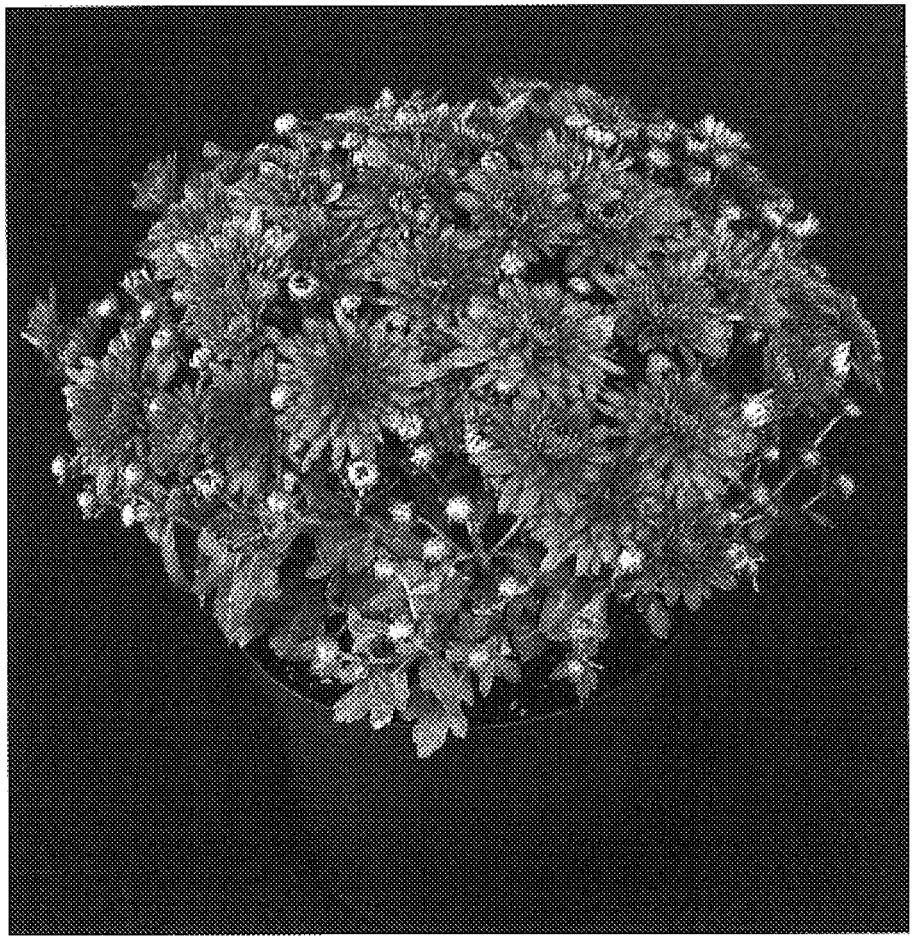

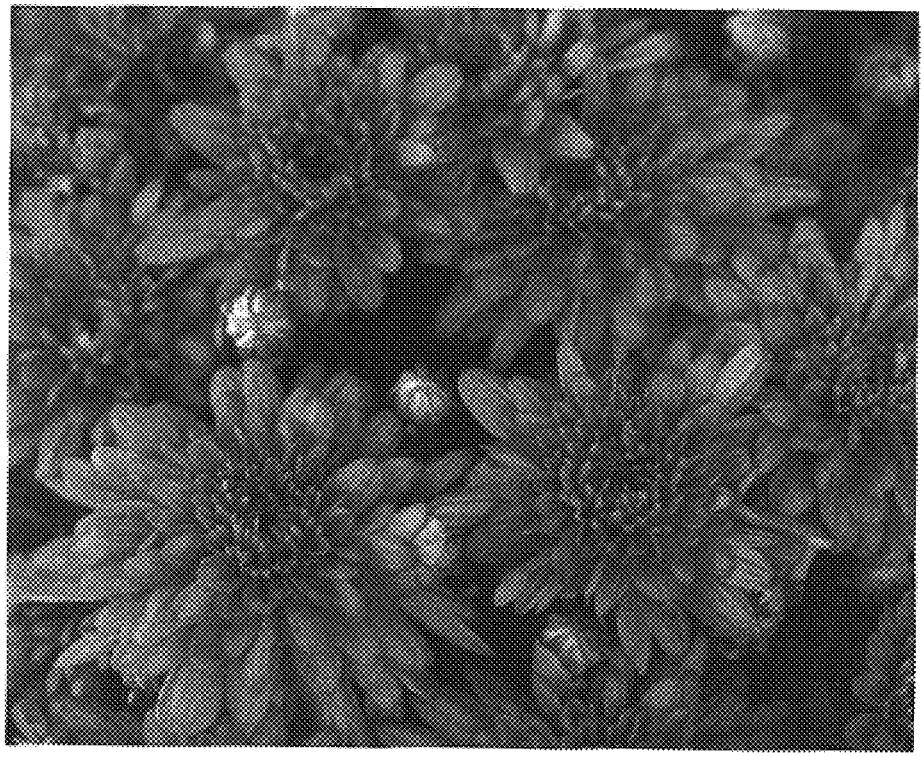

* * * * *